United States Patent [19]

Kumoi et al.

[11] Patent Number: 4,490,556
[45] Date of Patent: Dec. 25, 1984

[54] METHOD FOR PREPARING BIS[β-(N,N-DIMETHYLAMINO)ETHYL]ETHER

[75] Inventors: Sadakatsu Kumoi, Hikari; Hideo Sakka, Shinnanyo; Yukihiro Tsutsumi, Tokuyama, all of Japan

[73] Assignee: Toyo Soda Manufacturing Co., Ltd., Shinnanyo, Japan

[21] Appl. No.: 542,949

[22] Filed: Oct. 18, 1983

[30] Foreign Application Priority Data

Oct. 18, 1982 [JP] Japan .................................. 57-181407

[51] Int. Cl.³ ...................... C07C 85/00; C07C 85/24
[52] U.S. Cl. .................................................... 564/508
[58] Field of Search ........................................ 564/508

[56] References Cited

U.S. PATENT DOCUMENTS

| | | | |
|---|---|---|---|
| 3,426,072 | 2/1969 | Warner | 564/508 |
| 3,480,675 | 11/1969 | Poppelsdorf | 564/508 |
| 4,049,716 | 9/1977 | Collet | 564/508 X |
| 4,168,242 | 9/1979 | Soula | 564/508 X |
| 4,177,212 | 12/1979 | Poppelsdorf | 260/584 R |
| 4,247,482 | 1/1981 | Poppelsdorf | 564/508 |

FOREIGN PATENT DOCUMENTS

| | | | |
|---|---|---|---|
| 2010839A | 7/1979 | United Kingdom | 564/508 |
| 2045237A | 10/1980 | United Kingdom | 564/508 |

Primary Examiner—Paul F. Shaver
Attorney, Agent, or Firm—Armstrong, Nikaido, Marmelstein & Kubovcik

[57] ABSTRACT

A method for preparing bis[β-(N,N-dimethylamino)ethyl]ether characterized by performing a one stage reaction at a temperature of below 100° C. wherein vapor of sulfuric anhydride is being introduced into a mixed solution consisting of sodium N,N-dimethylaminoethoxide, N,N-dimethylethanolamine and dioxane.

7 Claims, No Drawings

METHOD FOR PREPARING BIS[β-(N,N-DIMETHYLAMINO)ETHYL]ETHER

DETAILED DESCRIPTION OF THE INVENTION

This invention relates to a method of preparing bis[β-(N,N-dimethylamino)ethyl]ether.

It has been known that bis[β-(N,N-dimethylamino)ethyl]ether (hereinafter abbreviated to etheramine) is a very useful compound as a catalyst of preparing polyurethane foam. The compound accelerates the reactions between the alcohol group and the isocyanate group and between water and isocyanate thereof. There have been various kinds of processes using miscellaneous starting materials for producing etheramine thereof, too. Among them, is a method utilizing a starting material available at relatively low cost, that is, a method of producing etheramine by reacting sodium N,N-dimethylaminoethoxide (hereinafter abbreviated to Na-DMAE) derived from N,N-dimethylethanolamine (hereinafter abbreviated to DMEA) with sulfuric anhydride ($SO_3$) is disclosed in British Patent Publication No. 2,010,839 (Japanese Kokai Patent Application No. Sho 54-95503) and British Patent Publication No. 2,045,237 (Japanese Kokai Patent Application).

The production method described in both literatures comprises basically the following reaction. That is to say, the starting material alkali metal N,N-dialkylaminoalkoxide is dissolved into N,N-dialkylaminoalkanol, the mixed solution into which an organic diluting/dispersing agent is added is recycled in a scrubber, the vapor of $SO_3$ accompanied with nitrogen gas is introduced into the vapor space of a reactor and the first stage reaction is carried out at a relatively low temperature of about 25° C. to form an intermediate. Next, etherification reaction of the second stage reaction is carried out at an elevated temperature of 100°–140° C. Then, the objective etheramine is produced by a so-called two stage reaction consisting of the above first stage and second stage reactions.

The reactor is designed so as to have an introduction portion of $SO_3$ vapor positioned at the vapor space of the reactor in order to avoid the stoppage of the introduction pipe of $SO_3$ vapor caused by burnt matters and solid Glauber's salt, which resulted from, and are deposited during the reaction. The reactor, is also equipped with a scrubber having a special structure to prevent the stoppage in the passage caused by solid matters. The reaction mixture taken out of the bottom of the reactor is recycled to the top of the scrubber by a pump to be subjected, and is vapor-liquid contact reaction.

As the organic diluting/dispersing agent, aliphatic hydrocarbons of carbon number 6–30 having boiling point of more than 90° C. and a property of not easily reacting with $SO_3$, and ethers such as tetrahydrofuran (boiling point 65°–67° C.), dioxane, monogrim, digrim etc. are exemplified from the main object of mitigating the reaction rate with $SO_3$ by diluting the starting material.

The inventors have reviewed the production of etheramine, by the two stage reaction, employing parafins and with blowing $SO_3$ vapor into the liquid phase of the reaction. The effect of parafins as the organic diluting/dispersing agents, has been proven in the examples. The inventors have observed a phenomenon wherein the reaction mixture discolored to deep-black and deep-black solid matters such as burnt matters etc. adhered as scale on the introduction pipe of $SO_3$ vapor. Also, the reaction yield of etheramine was 65% on basis of $SO_3$ and 61% on basis of DMEA. Accordingly, in case the producing method described in the literature concerned is industrially practiced, a reactor equipped with the scrubber and the attached facilities such as liquid recycling pump etc. is required in the aspect of apparatus and the reactor should be equipped with refrigerating facilities in order to control the reaction temperature at 20°–30° C. On the other hand, in the aspect of operation, the recycling of the reaction mixture containing the solid matters is required. Further, the adhesion of scale to vessel wall of piping path, resulting from this adhesion scrubber, pump etc. and the trouble of the stoppage are feared, of handling because the burnt matters resulting during the reaction and the reaction mixture containing solid matters and Glauber's salt which has become sludge-like due to containing them are handled.

Accordingly, it is desired to have a reaction method for producing etheramine which does not require special attached facilities such as a scrubber, etc., and, wherein the available reactor is employed. It is also desireable to have an industrially feasible reaction process of blowing $SO_3$ vapor directly into the liquid phase, wherein the phenomenon of scaling of the reaction product to the introduction pipe of the $SO_3$ vapor, the stoppage thereof, and the formation of the burned matters is eliminated. Also, from an economical standpoint, it is strongly desired for the production process to increase the yield of etheramine, based on DMEA, which is more expensive than $SO_3$.

As a result of elaborate studying, the method of producing etheramine in order to solve these problems, the inventors have found an unexpected and novel fact that the yield of etheramine based on not only $SO_3$ but also DMEA can be greatly improved by performing one stage reaction at a temperature of below 100° C. under introducing $SO_3$ vapor into the reaction mixture added with dioxane. In other words, this invention proposes a method for producing bis[β(N,N-dimethylamino)ethyl]ether characterized by performing one stage reaction at a temperature of below 100° C. wherein vapor of sulfuric anhydride is being introduced into a mixed solution consisted of sodium N,N-dimethylaminoethoxide, N,N-dimethylethanolamino and dioxane. Sodium N,N-dimethylaminoethoxide (Na-DMAE) employed in this invention can be produced by reacting N,N-dimethylethanolamine (DMEA) with sodium hydroxide, followed by distilling away water from the by-product outside of the reaction system. At this time, the reaction can be practiced in the presence of an azeotropic agent such as toluene and so on. Also, the Na-DMAE can be produced by DMEA with metal sodium. Likewise as the Na-DMAE, K-DMAE also can be employed as the starting material, but is not so advantageous as the starting material, for it becomes expensive at the cost thereof. The reaction is required to be performed in a state that Na-DMAE is homogeneously dissolved, and therefore the solubility of Na-DMAE, which is dissolved in DMEA and is subjected to the reaction, depends mainly on the mixed ratio to DMEA and the temperature. The amount of added DMEA is desired to be more than the amount that Na-DMAE is homogeneously dissolved at the reaction temperature, but 0.5–3 mol preferably 1–2 mol of DMEA per 1 mol of Na-DMAE is added, though it is not particularly limited. In case of less than 0.5 mol the solubility of Na-DMAE is not enough even at high reaction temperature region, and even if more than 3 mol is added, there does not arise a particularly advantageous effect in the aspect of yield etc., only increasing the amount of reaction mixture.

In this invention, the addition of organic solvent is mandatory in order to dilute Na-DMAE and to mitigate the violent reactivity of SO₃. As the organic solvent concerned, only dioxane is used. In the case of employing other various kinds of solvents such as pyridine, tri-n-butylamine, tetrahydrofuran and so on, the reaction mixture changes to black, burnt matters can not be depressed enough and the increase in the yield of etheramine is not satisfactory, too.

The reasons for the increase in the yield of etheramine which is found only in case of adding dioxane is unclear, but it is considered that there is something such as an effect more than diluting effect whose main effect lies in mitigating the reaction. The addition amount of dioxane is ordinarily 0.3–3 mol, preferably 0.6–2 mol per 1 mol of Na-DMAE. In case the addition amount is less than 0.3 mol, the yield of the product is lowered and unfavourable results in the aspect of the reaction arise. Also, even though more than 2 mol can be added, there is no favourable effect by further increasing the addition amount in the aspect of the reaction and it results in only increasing the amount of the reaction mixture. According to this invention, sulfuric anhydride (SO₃) can be subjected to the gas-liquid catalytic reaction without any scaling and stoppage in the front outlet of the introduction pipe, even though it is directly introduced into the liquid phase of the reaction mixture as SO₃ vapor. Accordingly, it is not necessary at all to adopt a complicated process such as introducing SO₃ vapor into the vapor phase portion of the reactor and then practicing the reaction with employing the scrubber. And any of the conventional reactor can be utilized for the reaction of this invention.

The amount of SO₃ is 0.3–0.6 mol, preferably 0.4–0.5 mol per 1 mol of Na-DMAE. In case of less than 0.3 mol, lots of the unreacted starting material Na-DMAE remains in the reaction mixture after the reaction and hence it is unfavourable in the aspect of reacting efficiency. In case of adding more than 0.6 mol, the yield of the product based on DMEA is lowered, so it is not favourable.

SO₃ is introduced into the reactor as SO₃ vapor usually in the form accompanied with nitrogen carrier gas by blowing nitrogen gas into a storage tank of SO₃. Accordingly, the supply ratio of nitrogen gas to SO₃ relates closely to the temperature of SO₃ storage tank and the period of introduction. Generally, the mixed gas having a ratio of 0.1–10 mol of nitrogen gas to 1 mol of SO₃ is supplied. The reaction period means the introduction period in other words, and it ranges over 0.5–10 hours. Although it is possible to perform the reaction within 0.5 hour, it is not favourable, because lots of nitrogen gas must be supplied as the carrier gas in order to supply SO₃ within such a short period. As, as the result, the amount of organic matters escaping with nitrogen gas outside of the reaction system is increased to enlarge the burden for treating exhaust gas. Although it is possible to perform the reaction over more than 10 hours, this results in the drop of productivity.

The process of this invention is usually performed at a reaction temperature of lower than 100° C., preferably 40°–100° C. in one stage reaction. Even in the so-called two stage reaction if the introduction reaction of SO₃ is really practiced at a low temperature in the region of 20°–30° C. and, after aging at the same temperature, the reaction is carried out at an elevated temperature of 100°–140° C. as seen in the conventional technique would be applied to the reaction system of this invention, any favourable result can not be obtained in the aspect of yield. The reaction is carried out above 40° C. which is possible to be cooled with water for industrial use and also below about 100° C. which is boiling point of dioxane. In case of below 40° C., the increase of yield is not recognized, the attached facilities for cooling are required and hence there is little industrial valuable significance. Then, in case of above 100° C., it is not favourable, because of the drop of yield. If the unreacted Na-DMAE remains in the system after the reaction, acid in an amount enough to neutralize it is added for recovering DMEA. The species of acid is not particularly restricted, but the use of cheap acid such as sulfuric acid, hydrochloric acid and so on is preferable.

After the completion of the reaction, dioxane, DMEA and etheramine are separated and recovered from the reaction mixture containing lots of Glauber's salt deposited as a by-product. It is possible to recover dioxane, DMEA and etheramine through distillation after adding a nonreactive organic compound having a boiling point of more than 210° C. into the reaction mixture as the pot-boiler, but the separating property of Glauber's salt and pot-boiler becomes a task and is not easy in the aspect of operativity, so it can not be said to be an excellent separating and recovering process.

The reaction mixture obtained by the reaction process based on this invention is supplied to a down-flow type thin film evaporating apparatus, the mixed solution consisting of mainly dioxane, DMEA and etheramine is recovered from the upper portion of this apparatus and then it is subjected to rectification, thereby etheramine of high purity is recovered.

As stated above, the process by this invention not only improves the yield of etheramine but also scarcely gives rise to the unfavourable by-reaction such as occurance of burnt organic matter, because the reaction mixture after the completion of the reaction is colored to light yellow. And, it can be said to be a method which entirely eliminates the troubles such as adhesion of scale on the introduction pipe of SO₃ vapor etc. located in the reaction mixture and the stoppage due to the solid matters and the like. Accordingly, without requiring the scrubber and the attached facilities such as recycle pump, refrigerating apparatus and the like, the production of etheramine by means of the universal reactor becomes feasible by introducing SO₃ vapor directly into the reaction mixture, and therefore this invention can be said to be a method of great industrial value in all aspects of apparatus, operativity, economy, productivity and so on.

This invention is hereinafter explained in detail by examples, but the method of this invention is not restricted by these examples. The yield of etheramine based on DMEA is calculated as follows.

$$\text{yield (\%)} = \frac{2 \times [\text{etheramine}]_f}{[\text{Na-DMAE}]_i + [\text{DMEA}]_i - [\text{DMEA}]_f} \times 100$$

[etheramine]$_f$: number of mol of resultant etheramine
[Na—DMAE]$_i$: number of mol of supplied DMAE
[DMEA]$_i$: number of mol of supplied DMEA
[DMEA]$_f$: number of mol of recovered DMEA

EXAMPLE 1

Into a glass-made four neck flask equipped with a stirrer, thermometer, refluxing condenser and vapor introduction pipe (the outlet of the vapor introduction pipe is located near the bottom of the reactor. The introduction pipe is connected to the supply source of $SO_3$ which is accompanied with nitrogen carrier gas), 166 g of DMEA, 134 g of Na-DMAE and 195 g of dioxane were added, heated with stirring up to 50° C. Nitrogen gas was blown into liquid $SO_3$ at a flow rate of 80-200 ml/min, and the mixed gas of nitrogen gas and $SO_3$ was introduced, under bubbling, into the lower portion of liquid phase of the reaction system through the vapor introduction pipe. Finally, 44.6 g of $SO_3$ was added over a period of 2 hours and twenty minutes. During this period, the temperature of the reaction was maintained at 50°-55° C. The obtained reaction mixture was tinged with light yellow clay color. After the completion of adding $SO_3$, the short column for distillation was connected to the reactor and a single distillation was carried out at the top temperature of 60°-100° C. under the reduced pressure of 300-10 mm/Hg to recover total weight 443 g of the mixed solution composed of DMEA, dioxane and etheramine. As a result of gas chromatographic analysis of the recovered solution, 67.8 g of etheramine was formed. The yield of etheramine was 76% based on $SO_3$ and also 84% based on DMEA.

EXAMPLE 2

Into the same reactor as in example 1, 166 g of DMEA, 134 g of Na-DMAE and 180 g of dioxane were added and heated with stirring up to 80° C. Blowing nitrogen gas into liquid $SO_3$ at a flow rate of 80-200 mol/min, the mixed gas of nitrogen and $SO_3$ was introduced, under bubbling, into the lower portion of liquid phase of the reaction system through the vapor introduction pipe. Finally, 47.0 g of $SO_3$ was supplied over a period of 4 hours to perform the reaction. During the period, the reaction temperature was kept at 80°-85° C. The reaction mixture after the completion of the reaction was tinged with slightly brown. After the completion of adding $SO_3$, 435 g of a distilled mixed solution consisted of mainly DMEA, dioxane and etheramine was recovered through the same operation as in example 1. As a result of gas-chromatographic analysing the recovered solution, 67.6 g of etheramine was formed. The yield of etheramine was 72% based on $SO_3$, and 79% based on DMEA.

COMPARATIVE EXAMPLE 1

Into the same reactor as in example 1, 174 g of DMEA, 134 g of Na-DMAE and 180 g of n-paraffin having carbon number of 14-15 were added and cooled to 25° C. Blowing nitrogen gas into liquid $SO_3$ at a flow rate of 50-100 ml/min, the mixed gas of nitrogen and $SO_3$ was introduced, under bubbling, into the lower portion of liquid phase of the reactor through the vapor introduction pipe. Finally, 44.6 g of $SO_3$ was supplied over a period of 3.5 hours. The reaction temperature during the addition of $SO_3$ was kept at 25°-28° C. After the completion of adding $SO_3$, the stirring was continued at the same temperature for 30 minutes and then the reaction mixture was heated up to 115° C. to undergo the reaction for 3 hours. The obtained reaction mixture was tinged with black. After the completion of the reaction, the short column for distillation was connected to the reactor and a single distillation was carried out at the top temperature of 80°-130° C. under the reduced pressure of 300-10 mm Hg to recover 274 g of a distillate containing DMEA, etheramine and small amount of n-paraffin. As a result of gas-chromatographic analysing this recovered solution, 58.0 g of etheramine was formed. The yield of etheramine was 65% based on $SO_3$ and also 61% based on DMEA.

COMPARATIVE EXAMPLE 2

Into the same reactor as in example 1, 174 g of DMEA, 134 g of Na-DMAE and 180 g of n-paraffin having carbon number of 14-15 were added and heated up to 50° C. Blowing nitrogen gas into liquid $SO_3$ at a flow rate of 70-180 ml/min, the mixed gas of nitrogen and $SO_3$ was introduced, under bubbling, into the lower portion of liquid phase of the reactor through the vapor introduction pipe. Finally, 46.2 g of $SO_3$ was supplied over a period of 4 hours to carry out the reaction. During the period, the reaction mixture was kept at a temperature range of 50°-55° C. After the completion of adding $SO_3$, 256 g of a distillate consisting of mainly DMEA, etheramine and small amount of n-paraffin was obtained through the same operation as in comparative example 1. As a result of gas-chromatographic analysing this distillate, the formation of 48.0 g of etheramine was identified. The yield of etheramine was 52% based on $SO_3$ and also 46% based on DMEA. As a result of gas-chromatographic analysing the solid of still residue after the single distillation which was dissolved into water, 0.4 g of etheramine was contained in the still residue. There was observed the adhesion of deep black solid precipitate on the outlet of $SO_3$ vapor introduction pipe after the completion of the reaction.

COMPARATIVE EXAMPLES 3-5

Into the same reactor as in example 1, 174 g of DMEA, 134 g of Na-DMAE and 203 g of the additive shown in Table 1 were added and heated up to 50° C. respectively. Blowing nitrogen gas into liquid $SO_3$ at a flow rate of 70-180 ml/min, the mixed gas of nitrogen and $SO_3$ were introduced, under bubbling, into the lower portion of liquid phase in the reactor through the vapor introduction pipe. During the period, the reaction mixture was kept at a temperature range of 50°-55° C. Finally, 46.2 g of $SO_3$ was supplied over a period of 3.5 hours to complete the reaction. The reactor was filled with pieces of column and a single distillation was carried out at the top temperature of 50°-100° C. under the reduced pressure of 500-10 mm Hg to give a distillate consisting of mainly DMEA, etheramine and the additive. A result of gas-chromatographic analysing this distillate was shown in Table 1. As a result of gas-chromatographic analysing the solid of still residue after the simple distillation which was dissolved into water, less than 0.1 g of etheramine was identified in every case.

TABLE 1

| Comparative Example | Additive | Yield of Etheramine (g) | Yield of Etheramine (%) | |
|---|---|---|---|---|
| | | | $SO_3$ base | DMEA base |
| 3 | pyridine | 65.6 | 71 | 61 |
| 4 | tri-n-butyl-amine | 43.4 | 47 | 57 |
| 5 | tetrahydro-furan | 61.9 | 67 | 62 |

What is claimed is:

1. A method for preparing bis[β-(N,N-dimethylamino)ethyl]ether which consists of introducing vapor of sulfuric anhydride into a mixed solution consisting of sodium N,N-dimethylaminoethoxide, N,N-dimethylethanolamine and dioxane to undergo a one stage reaction at a temperature not exceeding 100° C.

2. The method for preparing bis[β-(N,N-dimethylamino)-ethyl]ether recited in claim 1, wherein N,N-dimethylethanolamine is added in an amount of 0.5–3 mol per 1 mol of sodium N,N-dimethylaminoethoxide.

3. The method for preparing bis[β-(N,N-dimethylamino)ethyl]ether recited in claim 1, wherein dioxane is added in an amount of 0.3–3 mol per 1 mol of sodium N,N-dimethylaminoethoxide.

4. The method for preparing bis[β-(N,N-dimethylamino)ethyl]ether recited in claim 1, wherein sulfuric anhydride ($SO_3$) is introduced in the form of a single body or in the form of a mixture with nitrogen gas.

5. The method for preparing bis[β-(N,N-dimethylamino)ethyl]ether recited in claim 1, wherein sulfuric anhydride ($SO_3$) is introduced in an amount of 0.3–0.6 mol per 1 mol of sodium N,N-dimethylaminoethoxide.

6. The method for preparing bis[β-(N,N-dimethylamino)ethyl]ether recited in claim 4, wherein sulfuric anhydride ($SO_3$) is introduced in a form of the mixture with 0.1–10 mol of nitrogen gas per 1 mol of $SO_3$.

7. The method for preparing bis[β-(N,N-dimethylamino)ethyl]ether recited in claim 4, wherein sulfuric anhydride ($SO_3$) is introduced over the reaction period of 0.5–10 hours.

* * * * *

UNITED STATES PATENT AND TRADEMARK OFFICE
CERTIFICATE OF CORRECTION

PATENT NO. : 4,490,556

DATED : Dec. 25, 1984

INVENTOR(S) : Kumoi et al

It is certified that error appears in the above-identified patent and that said Letters Patent is hereby corrected as shown below:

Column 1, lines 15 - 16; delete "thereof, too".

Column 1, line 17; insert --there-- between "them," and "is".

Column 1, line 42; delete "so as"

Column 1, line 51; delete "to be" and insert --and is--.

Column 1, line 52; delete ", and is" and insert --to--.

Column 3, line 9; delete "concerned,".

Column 3, line 59; delete ", as the" and insert --a--.

Signed and Sealed this

Thirtieth Day of July 1985

[SEAL]

Attest:

DONALD J. QUIGG

Attesting Officer     Acting Commissioner of Patents and Trademarks